United States Patent
Cavin et al.

(10) Patent No.: US 8,119,587 B2
(45) Date of Patent: Feb. 21, 2012

(54) MICROCAPSULES

(75) Inventors: Laurent Cavin, Fechy (CH); Cedric Geffroy, Poitier (FR); Ian Michael Harrison, Poissy (FR); Jutta Hotz, Zurich (CH); Marion Mathys, Duebendorf (CH); Christian Quellet, Biel (CH)

(73) Assignee: Givaudan SA, Vernier (CH)

( * ) Notice: Subject to any disclaimer, the term of this patent is extended or adjusted under 35 U.S.C. 154(b) by 258 days.

(21) Appl. No.: 12/526,319

(22) PCT Filed: Feb. 6, 2008

(86) PCT No.: PCT/CH2008/000044
§ 371 (c)(1),
(2), (4) Date: Aug. 7, 2009

(87) PCT Pub. No.: WO2008/098387
PCT Pub. Date: Aug. 21, 2008

(65) Prior Publication Data
US 2010/0009893 A1    Jan. 14, 2010

(30) Foreign Application Priority Data
Feb. 13, 2007    (EP) .................................. 07290178

(51) Int. Cl.
*C11D 17/00*    (2006.01)
(52) U.S. Cl. ...................................................... 510/441
(58) Field of Classification Search .................... 510/441
See application file for complete search history.

(56) References Cited

U.S. PATENT DOCUMENTS
4,753,759 A * 6/1988 Fukuo et al. ................... 264/4.7
2003/0050220 A1 * 3/2003 Trinh et al. .................... 510/521

FOREIGN PATENT DOCUMENTS
GB    2133374 A    7/1984
WO    2006129252 A    12/2006

* cited by examiner

*Primary Examiner* — John Hardee
(74) *Attorney, Agent, or Firm* — Norris McLaughlin & Marcus, PA

(57) ABSTRACT

Microcapsules comprising a core of fragrance and a shell of aminoplast polymer, the composition of the shell being from 75-100% of a thermoset resin comprising 50-90%, preferably from 60-85%, of a terpolymer and from 10-50%, preferably from 10-25%, of a polymeric stabilizer; the terpolymer comprising: (a) from 20-60%, preferably 30-50% of moieties derived from at least one polyamine, (b) from 3-50%, preferably 5-25% of moieties derived from at least one aromatic polyol; and (c) from 20-70%, preferably 40-60% of alkylene or alkylenoxy moieties having 1 to 6 methylene units, preferably 1 to 4 methylene units and most preferably 1 methylene unit; the microcapsules additionally optionally comprising up to 25%, preferably up to 10% of a cationic polymer. The microcapsules are useful for the storage and dissemination of fragrance in various products, such as laundry products and fabric care products.

19 Claims, No Drawings

MICROCAPSULES

This is an application filed under 35 USC 371 of PCT/CH2008/000044.

This invention is concerned with liquid compositions containing stable, water-dispersible, electrically-charged and highly fabric-substantive microcapsules containing microencapsulated ingredients, such as fragrances, flavours, malodour counteractant, pro-fragrances or mixtures thereof, intended for use in consumer products such as detergents and conditioners, and in particular which can control the activation and diffusion of the ingredients in time in response to an external stimulus that is mechanical breakage and/or heat.

It is well known that ingredients such as fragrances, insecticides, malodour counteracting substances, fungicides and mildewicides, and the like may be encapsulated in a microcapsule comprising a solid shell or membrane, which protects them from their immediate environment and acts as means for their controlled release. A popular and convenient method of producing such encapsulated formulations consists of dispersing the ingredient in a liquid and creating a polymeric membrane on the surface of the droplets. Examples of suitable processes include the simple and complex coacervation of gelatine with gum Arabic followed by cross-linking with glutaraldehyde. More generally, many polymers or mixtures of polymers capable of forming insoluble complexes under specific conditions can be used to form such interfacial membranes by so-called polymer phase separation process.

Alternatively, interfacial membranes can be produced by the polycondensation of various co-monomers and macromers. The polycondensation of urea with formaldehyde (UF), melamine (2,4,6-triamino-1,3,5-triazine) with formaldehyde (MF) to form so-called aminoplast microcapsules is the most popular among these processes, leading to shells consisting of highly cross-linked resins (also known as thermoset resin). Aminoplast thermosets based on benzoguanamine and formaldehyde, as well as on glycoluril and formaldehyde, are used in the coatings industry. On the other hand, microcapsules having thermoplastic polyester, polyamides, etc. shells are also well known, although most of these latter materials more prone to plasticization and leakage than those derived from thermoset resins.

These established processes essentially convert emulsions consisting of a dispersed oil phase containing the ingredient to be encapsulated and a continuous water phase into a suspension of solid beads consisting of a core surrounded by a membrane, whose permeability depends on a number of factors, including the extent of cross-linking, and/or the thickness of said membrane.

When applied to fragrances, these microcapsules are typically used for generating surprising sensory effects, such as an increased perfume intensity, or impact, at some point in time when the microcapsules are broken by the action of pressure or rubbing. This strategy is used in so-called "scratch-and-sniff" systems. They may be used, optionally in conjunction with non-encapsulated perfume, in liquid consumer products.

However, when used in consumer products, these capsules generally suffer from serious stability issues, such as wall rupture under the effect of osmotic pressure or extraction of the perfume by the conjugated action of the surfactants and external, non-encapsulated perfume present in the product base, especially after prolonged storage at elevated temperatures. This leads to a loss of perfume. This can be circumvented by reinforcing the wall of the microcapsules by various means, such as increasing the cross-linking density of the wall or applying a coating to it. However, this leads generally to an increase of the load required to break the microcapsules and, consequently, makes the release of the encapsulated fragrance more difficult.

A further problem encountered in the art is the presence of free formaldehyde, or the generation of formaldehyde, especially in acidic conditions. Formaldehyde is a very undesirable substance, and its emission should be minimal, preferably non-existent.

A desirable goal is a product having both an external, non-encapsulated fragrance and a microencapsulated fragrance, the latter being different in strength and quality from the former. The capsules should be sufficiently stable over time in aqueous consumer products containing high levels of surfactants and salts, yet with a suitably high degree of frangibility that they can provide, even after prolonged storage at elevated temperatures, the release of different olfactive impressions when submitted to light mechanical stresses, such as those encountered in folding, putting on, wearing and taking off a garment.

Another desirable goal is a product having a reduced level of free and nascent formaldehyde.

It has now been found that it is possible to prepare microcapsules comprising a melamine-formaldehyde aminoplast terpolymer containing polyol moieties, and especially aromatic polyol moieties, which fulfil substantially all of the above requirements. There are therefore provided microcapsules comprising a core of fragrance and a shell of aminoplast polymer, the composition of the shell being from 75-100% of a thermoset resin comprising 50-90%, preferably from 60-85%, of a terpolymer and from 10-50%, preferably from 10-25%, of a polymeric stabilizer; the terpolymer comprising:

(a) from 20-60%, preferably 30-50% of moieties derived from at least one polyamine,
(b) from 3-50%, preferably 5-25% of moieties derived from at least one aromatic polyol; and
(c) from 20-70%, preferably 40-60% of moieties selected from the group consisting of alkylene and alkylenoxy moieties having 1 to 6 methylene units, preferably 1 to 4 methylene units and most preferably 1 methylene unit, dimethoxy methylene and dimethoxy methylene;

the microcapsules additionally optionally comprising up to 25%, preferably up to 10% of a cationic polymer.

In this description, unless otherwise specifically stated, all percentages are by weight.

By "moiety" is meant a chemical entity, which is part of the terpolymer and which is derived from a particular molecule. The terpolymer hereinabove described may be any terpolymer comprising the moieties hereinabove described, and it may be prepared by any of the many suitable methods known to the art. Example of suitable polyamine moieties include, but are not limited to, those derived from urea, melamine, 3-substituted 1,5-diamino-2,4,6-triazin and glycouril. Examples of suitable aromatic polyol moieties include, but are not limited to, those derived from phenol, 3,5-dihydroxy toluene, Bisphenol A, resorcinol, hydroquinone, xylenol, polyhydroxy naphthalene and polyphenols produced by the degradation of cellulose and humic acids.

The use of the term "derived from" does not necessarily mean that the moiety in the terpolymer is directly derived from the substance itself, although this may be (and often is) the case. In fact, one of the more convenient methods of preparing the terpolymer involves the use of alkylolated polyamines as starting materials; these combine in a single molecule both the moieties (a) and (c) mentioned hereinabove.

Suitable alkylolated polyamines encompass mixtures of mono- or polyalkylolated polyamines, which in turn may be partially alkylated with alcohols having from 1 to 6 methylene units. Alkylated polyamines especially suitable for the sake of the present invention include mono- and polymethylol-urea pre-condensates, such as those commercially available under the Trade Mark URAC (ex Cytec Technology Corp.) and/or partially methylated mono- and polymethylol-1,3,5-triamino-2,4,6-triazine pre-condensates, such as those commercially available under the Trade Mark CYMEL (ex Cytec Technology Corp.) or LURACOLL (ex BASF), and/or mono- and polyalkylol-benzoguanamine pre-condensates, and/or mono- and polyalkylol-glycouril pre-condensates. These alkylolated polyamines may be provided in partially alkylated forms, obtained by addition of short chain alcohols having typically 1 to 6 methylene units. These partially alkylated forms are known to be less reactive and therefore more stable during storage. Preferred polyalkylol-polyamines are polymethylol-melamines and polymethylol-1-(3,5-dihydroxy-methylbenzyl)-3,5-triamino-2,4,6-triazine.

Alternatively, poly[N-(2,2-dimethoxy-1-hydroxy)] polyamines can be used, including di-[N-(2,2-dimethoxy-1-hydroxy)]urea, tri-[N-(2,2-dimethoxy-1-hydroxy)]melamin, tetra-[N-(2,2-dimethoxy-1-hydroxy)]glycouryl and di-[N-(2,2-dimethoxy-1-hydroxy)]benzoguanidin.

The polymeric stabiliser prevents the microcapsules from agglomerating, thus acting as a protective colloid. It is added to the monomer mixture prior to polymerisation, and this results in its being partially retained by the polymer, while another part passes into the continuous phase.

Particular examples of suitable polymeric stabilizers include acrylic copolymers bearing sulfonate groups, such as those available commercially under the trade mark LUPASOL (ex BASF), such as LUPASOL PA 140 or LUPASOL VFR; copolymers of acrylamide and acrylic acid, copolymers of alkyl acrylates and N-vinylpyrrolidone, such as those available under the trade mark Luviskol (e.g. LUVISKOL K 15, K 30 or K 90 ex BASF); sodium polycarboxylates (ex Polyscience Inc.) or sodium poly(styrene sulfonate) (ex Polyscience Inc.); vinyl and methyl vinyl ether-maleic anhydride copolymers (e.g. AGRIMER™ VEMA™ AN, ex ISP), and ethylene, isobutylene or styrene-maleic anhydride copolymers. Hence the preferred polymer stabilizers are anionic polyelectrolytes.

Optionally, the microcapsules may be coated with a cationic polymer. The cationic polymer allows partial or complete neutralization of the negative electrical charge borne by the microcapsules, or even the conversion of the negatively-charged microcapsules into positively-charged microcapsules.

Preferred cationic polymers comprise cationic cellulose derivatives, such as those available under the Trade Mark UCARE (ex Amerchol), and quaternized gums, such as quaternized guar gums available under the Trade Mark JAGUAR (ex Rhodia), polyethylene imine, such as those available commercially under the Trade Mark LUPASOL (ex BASF), cationic polyacrylates and acrylamides, gelatine and quaternized protein hydrolysates, and quaternized amino silicones.

Other cationic compounds that can be used include the Polyquaternium range, all of which have a plurality of quaternary ammonium groups, polymeric species such as diallyl dimethyl ammonium chloride/acrylamide polymers, for example, those available under the Trade Mark MERQUAT (ex Nalco) and copolymers of vinyl pyrrolidone and quaternized dimethyaminoalkyl methacrylate, for example, those available under the Trade Mark GAFQUAT HS 50 and HS 100 (ex ISP).

Microcapsules of the type hereinabove described are provided in the form of aqueous slurry, having typically 20 to 50% solids content, and more typically 30 to 45% solid content, where the term "solids content" refers to the total weight of the microcapsules. The average size of the microcapsules may range between 1 micrometer to 100 micrometers, or more, depending on the mixing shear stress applied to the system during microcapsule formation. The selection of the most appropriate microcapsule size range and size distribution depends on the application envisioned. In the case where the microcapsules are to be used in laundry products, it has been found that microcapsules having size ranging from 20 to 60 micrometers offer optimal performance in terms of deposition and olfactive impact when rubbed with small to moderate shear stress. This is a surprising finding, as the prior art preferably claims microcapsules having size smaller then 20 micrometers for such applications.

The slurry may contain formulation aids, such as stabilizing and viscosity control hydrocolloids, biocides, and additional formaldehyde scavengers.

Typically, hydrocolloids are used to improve the colloidal stability of the slurry against coagulation, sedimentation and creaming. The term "hydrocolloid" refers to a broad class of water-soluble or water-dispersible polymers having anionic, cationic, zwitterionic or non-ionic character. Hydrocolloids useful for the sake of the present invention encompass: polycarbohydrates, such as starch, modified starch, dextrin, maltodextrin, and cellulose derivatives, and their quaternized forms; natural gums such as alginate esters, carrageenan, xanthanes, agar-agar, pectines, pectic acid, and natural gums such as gum arabic, gum tragacanth and gum karaya, guar gums and quaternized guar gums; gelatine, protein hydrolysates and their quaternized forms; synthetic polymers and copolymers, such as poly(vinyl pyrrolidone-co-vinyl acetate), poly(vinyl alcohol-co-vinyl acetate), poly((met) acrylic acid), poly(maleic acid), poly(alkyl(meth)acrylate-co-(meth)acrylic acid), poly(acrylic acid-co-maleic acid)copolymer, poly(alkyleneoxide), poly(vinylmethylether), poly(vinylether-co-maleic anhydride), and the like, as well as poly-(ethyleneimine), poly((meth)acrylamide), poly(alkyleneoxide-co-dimethylsiloxane), poly(amino dimethylsiloxane), and the like, and their quartenized forms;

Typical formaldehyde scavengers comprise compounds capable of binding free formaldehyde in aqueous media, such as sodium sulfite, melamine, glycine, and carbohydrazine. However, when the microcapsules are aimed to be used in products having low pH, such as fabric care conditioners, formaldehyde scavengers are preferably selected from beta diketones, such as beta-ketoesters, or from 1,3-diols, such as propylene glycol. Preferred beta-ketoesters comprise alkyl-malonates, alkyl aceto acetates and polyvinyl alcohol aceto acetates.

The microcapsules according to the invention are further characterized by a nominal shell to core mass ratio lower than 15%, preferably lower than 10% and most preferably lower than 5%. Hence, the microcapsules may have extremely thin and frangible shells.

The shell to core ratio is obtained by measuring the effective amount of encapsulated perfume oil microcapsules that have been previously washed with water and separated by filtration. This is achieved by extracting the wet microcapsule cake by microwave-enhanced solvent extraction and subsequent gas chromatographic analysis of the extract.

Compared to the aminoplast microcapsules of the prior art, the microcapsules of the present invention display a number of unexpected advantages. These include:

- a significantly lower level of equilibrium formaldehyde levels in acidic media,
- the ability to accommodate a much wider range of fragrance compositions than has previously been the case, including fragrance compositions whose encapsulation has been difficult or even impossible by known methods,
- the preparation of these microcapsules requires much less of the alkylolated polyamine starting materials hereinabove mentioned than do conventional microcapsules. The microcapsules require less than 40% of the alkylolated polyamines starting materials usually required to obtain the same yield of encapsulation (as defined as the ratio of encapsulated fragrance to total fragrance provided before encapsulation takes place). This contributes significantly to decreasing the level of residual and equilibrium free formaldehyde in the system,
- the overall amount of shell material required to build up a stable microcapsule is considerably reduced, leading to thinner capsule walls and much better frangibility to stability balance than has been hitherto achievable. This leads to a surprisingly high perfume retention, compared to the very small thickness of the microcapsule wall,
- the microcapsules are much less prone to plasticization by external, non-encapsulated fragrances,
- the microcapsules show a much lower level of the residual or equilibrium free formaldehyde than that which would be expected, based on the mass reduction of the encapsulated materials only. This hints at better neutralisation of the unreacted methylol groups of the resins and more favourable polycondensation equilibrium constant. This advantage helps make the microcapsules of the invention highly suitable for laundry products, specifically, powder, liquid detergent and liquid fabric softeners,
- the microcapsules can be used in the anionic form, i.e. without any cationic coating, in fabric care conditioners, without impeding their substantivity on cotton, polyester and other fabrics. This is a surprising results, which cannot be anticipated from the prior art.

The microcapsule slurry according to the invention is furthermore capable of releasing electrically-charged microcapsules, characterized by an absolute zeta-potential ranging from 0.1 mV to 100 mV when dispersed in deionised water.

By "zeta-potential" ($\zeta$) is meant the apparent electrostatic potential generated by any electrically charged objects in solution, as measured by specific measurement techniques. A detailed discussion of the theoretical basis and practical relevance of the zeta-potential can be found, e.g., in "Zeta Potential in Colloid Sciences" (Robert. J. Hunter; Academic Press, London 1981, 1988). The zeta-potential of an object is measured at some distance from the surface of the object and is generally not equal to and lower than the electrostatic potential at the surface itself. Nevertheless, its value provides a suitable measure of the capability of the object to establish electrostatic interactions with other objects present in the solution, such as surfactants, polyelectrolytes and surfaces. The zeta-potential is a relative measurement and its value depends on the way it is measured. In the present case, the zeta-potential of the microcapsules is measured by the so-called phase analysis light scattering method, using a Zeta-PALS instrument (ex Brookhaven Instruments Corporation). The zeta-potential of a given object may also depend on the quantity of ions present in the solution. The values of the zeta-potential specified in the present application are measured either in deionised water, where only the counter-ions of the charged microcapsules are present, or in wash liquor, where other charged species are present. By "absolute zeta-potential" ($|\zeta|$) is meant the absolute value of the zeta-potential without reference to its (positive or negative) sign. Hence, negatively-charged objects having a zeta-potential of $-10$ mV and positively charged species having a zeta-potential of $+10$ mV have the same absolute zeta-potential.

In a particular embodiment, a composition utilising the microcapsules hereinabove described is characterized by its ability to deliver microcapsules for fabric care conditioners, the microcapsules having a negative zeta-potential ranging from $-0.1$ mV and $-100$ mV when dispersed in deionised water.

The microcapsules are highly frangible, by which is meant the ability of the dry microcapsules according to the invention to break and release the encapsulated perfume under the action of a normal bursting force not superior to 9 mN for microcapsules having a diameter of 60 micrometers and not superior to 3 mN for microcapsules having a diameter of 35 micrometers, which corresponds to a bursting pressure not higher than $6 \times 10^6$ MPa. Typically, the bursting pressure of microcapsules according to the present invention does not exceed 1 to 10 MPa, preferably 4 to 7 MPa. Both bursting force and bursting pressure may be measured by various methods, such as a nano-indentation test, as described in Example 3, or an osmotic rupture test. These aforementioned forces refer to the ones currently applied to a garment when it is folded, put on, worn or taken off.

By "dry microcapsule" is meant microcapsules that have been submitted to usual drying conditions such as those prevailing during line drying or tumble drying.

Microcapsules for use in liquid, aqueous fabric care conditioners constitute a particular embodiment of the present invention and are obtained by following the steps of:

1. Adding and dissolving alkylolated polyamine or poly[N-(2,2-dimethoxy-1-hydroxy)]polyamine pre-condensates and polymer stabilizer in deionised water under moderate shear mixing, 1A. Optionally heating above mixture at 85° C. for 90 minutes, 2. Adding a fragrance oil to the above solution and emulsifying the system under moderate to high shear mixing, whereby the stirring speed and the geometry of the mixer is defined as a function of the desired average microcapsule size range and microcapsule size distribution, 3. Adjusting the pH to a range of 3 to 4.5 by adding formic acid, and the temperature to a range of 30 to 45° C., for a duration time of 1 to 3 hours, while keeping same stirring rate, 4. While performing Step 3, adding an aromatic polyol to the reaction medium, either at the beginning or at the end of Step 3, or continuously, or step by step during Step 3.

5. Heating the mixture up to 50 to 90° C. for a duration time of 1 to 5 hours.

5A. While performing Step 5, optionally add an aromatic polyol to the reaction mixture, 6. Cooling the system to room temperature.

In a typical composition according to the invention, the typical amount of perfume oil added to the reaction medium that forms the terpolymer is between 20 and 50 wt %, preferably between 30 and 40 wt %, most preferably between 35 and 40 wt % of the total mix. The composition range of the other ingredients entering in the microencapsulation is given below for a nominal perfume concentration of 38 wt %. However, it will be obvious of anybody skilled in the art that modifying this nominal perfume oil level will require optimization of the levels of the other ingredients.

Hence, for a nominal perfume oil concentration of 38 wt %, the composition of the reaction medium will preferably be as follows:

1 to 10 wt %, preferably 2 to 8 wt % and most preferably 3 to 4 wt % of alkylolated polyamines,
0.1 to 3 wt %, preferably 0.3 to 2 wt % and most preferably 0.5 to 1.5 wt % of aromatic polyols,
0.1 to 3 wt %, preferably 0.3 to 2 wt % and most preferably 0.5 to 1.5 wt % of stabilizing polymer.

the balance being water.

Fragrance materials for use in compositions of the present invention may be selected from natural products such as essential oils, absolutes, resinoids, resins, concretes, and synthetic perfume components such as hydrocarbons, alcohols, aldehydes, ketones, ethers, acids, acetals, ketals and nitriles, including saturated and unsaturated compounds, aliphatic, carbocyclic and heterocyclic compounds, or precursors of any of the above. Other examples of odorant compositions which may be used are described in H 1468 (United States Statutory Invention Registration).

Examples of preferred fragrance components are any of those fragrances selected from Agrumex, Aldron, Ambrettolide, Ambroxan, benzyl cinnamate, benzyl salicylate, Boisambrene, cedrol, cedryl acetate, Celestolide/Crysolide, Cetalox, citronellyl ethoxalate, Fixal, Fixolide, Galaxolide, Guaiacwood Acetate, cis-3-hexenyl salicylate, hexyl cinnamic aldehyde, hexyl salicylate, Iso E Super, linalyl benzoate, linalyl cinnamate, linalyl phenyl acetate, Javanol, methyl cedryl ketone, Moskene, Musk, Musk Ketone, Musk Tibetine, Musk Xylol, Myraldyl Acetate, nerolidyl acetate, Novalide, Okoumal, para-cresyl caprylate, para-cresyl phenyl acetate, Phantolid, phenyl ethyl cinnamate, phenyl ethyl salicylate, Rose Crystals, Rosone, Sandela, tetradecanitrile, Thibetolide, Traseolide, Trimofix O, 2-methylpyrazine, acetaldehyde phenylethyl propyl acetal, acetophenone, alcohol C6 (in the following the notation Cn comprises all substances having n carbon atoms and one hydroxyl function), alcohol C8, aldehyde C6 (in the following the notation Cn encompasses all isomers having n carbon atoms and one aldehyde function), aldehyde C7, aldehyde C8, aldehyde C9, nonenylic aldhyde, allyl amyl glycolate, allyl caproate, amyl butyrate, aldehyde anisique, benzaldehyde, benzyl acetate, benzyl acetone, benzyl alcohol, benzyl butyrate, benzyl formate, benzyl iso-valerate, benzyl methyl ether, benzyl propionate, Bergamyl Acetate, butyl acetate, camphor, 3-methyl-5-propyl-2-cyclohexenone, cinnamic aldehyde, cis-3-hexenol, cis-3-hexenyl acetate, cis-3-hexenyl formate, cis-3-hexenyl iso-butyrate, cis-3-hexenyl propionate, cis-3-hexenyl tiglate, citronellal, citronellol, citronellyl nitrile, 2-hydroxy-3-methyl-2-cyclopenten-1-one, cuminic aldehyde, Cyclal C, acetic acid (cycloheyloxy)-2-propenylester, damascenone, alpha-damascone, beta-damascone, decahydro beta-napthyl formate, diethyl malonate, dihydro-jasmone, dihydro-linalool, dihydro-myrcenol, dihydro-terpineol, dimethyl anthranilate, dimethyl benzyl carbinol, dimethyl benzyl carbinyl acetate, dimethyl octenone, Dimetol, dimyrcetol, estragole, ethyl acetate, ethyl aceto-acetate, ethyl benzoate, ethyl heptoate, ethyl linalool, ethyl salicylate, ethyl-2-methyl butyrate, eucalyptol, eugenol, fenchyl acetate, fenchyl alcohol, 4-phenyl-2,4,6-trimethyl 1,3-dioxane, methyl 2-octynoate, 4-isopropylcyclohexanol, 2-sec-butylcyclohexanone, styralyl acetate, geranyl nitrile, hexyl acetate, alpha-ionone, iso-amyl acetate, iso-butyl acetate, isocyclocitral, dihydroisojasmone, iso-menthone, iso-pentyrate, iso-pulegol, cis-jasmone, laevo-carvone, phenylacetaldehyde glycerylacetal, carbinic acid 3-hexenyl methyl ether, 1-methyl-cyclohexa-1,3-diene, linalool, linalool oxide, 2-ethyl ethyl ester pentanoate, 2,6-dimethyl-5-heptenal, menthol, menthone, methyl acetophenone, methyl amyl ketone, methyl benzoate, alpha-methyl cinnamic aldehyde, methyl heptenone, methyl hexyl ketone, methyl para cresol, methyl phenyl acetate, methyl salicylate, Neral, Nerol, 4-tert-pentyl-cyclohexanone, para-cresol, para-cresyl acetate, para-t-butyl cyclohexanone, para-toluoyl aldehyde, phenyl acetaldehyde, phenyl ethyl acetate, phenyl ethyl alcohol, phenyl ethyl butyrate, phenyl ethyl formate, phenyl ethyl iso butyrate, phenyl ethyl propionate, phenyl propyl acetate, phenyl propyl aldehyde, tetrahydro-2,4-dimethyl-4-pentyl-furan, 4-methyl-2-(2-methyl-1-propenyl)tetrahydropyran, 5-Methyl-3-heptanone oxime, styralyl propionate, styrene, 4-methylphenylacetaldehyde, terpineol, terpinolene, tetrahydro-linalool, tetrahydro-myrcenol, trans-2-hexenal, verdyl acetate and Viridine.

In a preferred embodiment of the present invention, the encapsulated fragrance comprises at least 70 wt % of fragrance components having a loss factor higher than $10^2$ Pa ppm, most preferably higher than $10^4$ Pa ppm. The term "Loss Factor" refers to a parameter that is related to the losses of fragrance material during drying and is defined as the product of the pure component vapour pressure (Pa) and the water solubility (ppm) at room temperature. Vapour pressures and water solubility data for commercially available fragrance components are well known and so the Loss Factor for a given fragrance component may be easily calculated. Alternatively, vapour pressure and water solubility measurements may be easily taken using techniques well known in the art. Vapour pressure of fragrance components may be measured using any of the known quantitative headspace analysis techniques, see for example Mueller and Lamparsky in Perfumes: Art, Science and Technology, Chapter 6 "The Measurement of Odors" at pages 176-179 (Elsevier 1991). The water solubility of fragrances may be measured according to techniques known in the art for the measurement of sparingly water-soluble materials. A preferred technique involves the formation of a saturated solution of a fragrance component in water. A tube with a dialysed membrane is placed in the solution such that after equilibration an idealised solution is formed within the tube. The tube may be removed and the water solution therein extracted with a suitable organic solvent to remove the fragrance component. Finally the extracted fragrance component may be concentrated and measured, for example using gas chromatography. Other methods of measuring fragrances are disclosed in Gygax et al, Chimia 55 (2001) 401-405.

Preferred fragrances having high loss factor may be selected from 2-methylpyrazine, acetaldehyde phenylethyl propyl acetal, acetophenone, alcohol C6 (in the following the notation Cn comprises all substances having n carbon atoms and one hydroxyl function), alcohol C8, aldehyde C6 (in the following the notation Cn encompasses all isomers having n carbon atoms and one aldehyde function), aldehyde C7, aldehyde C8, aldehyde C9, nonenylic aldhyde, allyl amyl glycolate, allyl caproate, amyl butyrate, aldehyde anisique, benzaldehyde, benzyl acetate, benzyl acetone, benzyl alcohol, benzyl butyrate, benzyl formate, benzyl iso-valerate, benzyl methyl ether, benzyl propionate, bergamyl acetate, autyl acetate, camphor, 3-methyl-5-propyl-2-cyclohexenone, cinnamic aldehyde, cis-3-hexenol, cis-3-hexenyl acetate, cis-3-hexenyl formate, cis-3-hexenyl iso-butyrate, cis-3-hexenyl propionate, cis-3-hexenyl tiglate, citronellal, citronellol, citronellyl nitrile, 2-hydroxy-3-methyl-2-cyclopenten-1-one, cuminic aldehyde, cyclal C, acetic acid (cycloheyloxy)-2-propenylester, damascenone, alpha-damascone, beta-damascone, diethyl malonate, dihydro jasmone, dihydro linalool, dihydro myrcenol, dihydro terpineol, dimethyl anthranilate, dimethyl benzyl carbinol, dimethyl benzyl carbinyl acetate, dimethyl octenone, dimetol, dimyrcetol, estragole, ethyl acetate, ethyl aceto acetate, ethyl benzoate, ethyl heptoate, ethyl linalool, ethyl salicylate, ethyl-2-methyl butyrate, eucalyptol, eugenol, fenchyl Acetate, fenchyl alcohol, 4-Phenyl-2,4,6-trimethyl 1,3-dioxane, methyl 2-octynoate, 4-isopropylcyclohexanol, 2-sec-butylcyclohexanone, styralyl acetate, geranyl nitrile, hexyl acetate, alpha-ionone, iso-amyl acetate, iso-butyl acetate, iso-cyclocitral, dihydroisojasmone, iso-menthone, iso-pentyrate, iso-pulegol, cis-jasmone, laevo carvone, phenylacetaldehyde glycerylacetal, carbinic acid 3-hexenyl methyl ether, 1-methyl-cyclohexa-1,3-diene, linalool, linalool oxide, 2,6-dimethyl-5-heptenal, menthol, menthone, methyl acetophenone, methyl amyl ketone, methyl benzoate, methyl cinnamic aldehyde alpha, methyl heptenone, methyl hexyl Ketone, methyl para-cresol, methyl phenyl acetate, methyl salicylate, neral, nerol, 4-tert-pentyl-cyclohexanone, para-cresol, para-cresyl acetate, para-t-butyl cyclohexanone, para-tolyl aldehyde, phenyl acetaldehyde, phenyl ethyl acetate, phenyl ethyl alcohol, phenyl ethyl butyrate, phenyl ethyl formate, phenyl ethyl iso-butyrate, phenyl ethyl propionate, phenyl propyl acetate, phenyl propyl aldehyde, tetrahydro-2,4-dimethyl-4-pentyl-furan, 4-methyl-2-(2-methyl-1-propenyl)tetrahydropyran, 5-methyl-3-heptanone oxime, styralyl propionate, styrene, 4-methylphenylacetaldehyde, terpineol, terpinolene, tetrahydro linalool, tetrahydro myrcenol, trans-2-hexenal, and Viridine.

In a further specific embodiment of the present invention, the fragrance components may have an odour value higher than 10,000. The odor value is defined as the standard headspace concentration $HS_i^o$ of odorant in thermodynamic equilibrium with this odorant in the standard state (278.15 K, 1 atmosphere), expressed in microgram/l headspace, divided by the olfactory threshold of this odorant (in microgram/l headspace) as measured by olfactometry. The standard headspace concentration is related to the vapor pressure of the pure ingredient by the equation:

$$HS_i^o \equiv \frac{m_i^*}{RT} p_i^o$$

where $m_i^*$ is the molar mass of the odorant, R is the gas constant, T the absolute temperature given in Kelvin and $p_i^o$ the standard vapor pressure given in atmosphere.

Precursor of fragrance components may also be provided in fragrance materials in the present invention. Precursors are compounds that, upon cleavage under activating conditions such as light, enzymes, elevated temperature or acidic or alkaline pH-values, provide compounds having fragrance characteristics.

Furthermore, other organoleptic materials may be used in admixture with fragrance ingredients, for example, odour-masking agents, insect repellents and the like.

The amount of fragrance possible to be micro-encapsulated is generally superior to 85 wt %, and even superior to 95 wt %, based on dry material, with a micro-encapsulation yield close or superior to 80 wt %, even for the very volatile components having a Loss Factor of greater than $10^2$ Pa ppm. The term "Loss Factor" refers to a parameter that is related to the losses of fragrance material during drying and is defined as the product of the pure component vapour pressure (Pa) and the water solubility (ppm) at room temperature. Vapour pressures and water solubility data for commercially available fragrance components are well known and so the Loss Factor for a given fragrance component may be easily calculated. Alternatively, vapour pressure and water solubility measurements may be easily taken using techniques well known in the art. Vapour pressure of fragrance components may be measured using any of the known quantitative headspace analysis techniques, see for example Mueller and Lamparsky in Perfumes: Art, Science and Technology, Chapter 6 "The Measurement of Odors" at pages 176-179 (Elsevier 1991). The water solubility of fragrances may be measured according to techniques known in the art for the measurement of sparingly water-soluble materials. A preferred technique involves the formation of a saturated solution of a fragrance component in water. A tube with a dialysed membrane is placed in the solution such that after equilibration an idealised solution is formed within the tube. The tube may be removed and the water solution therein extracted with a suitable organic solvent to remove the fragrance component. Finally the extracted fragrance component may be concentrated and measured, for example using gas chromatography. Other methods of measuring fragrances are disclosed in Gygax et al, Chimia 55 (2001) 401-405.

In a further specific embodiment, the fragrance components may have a ClogP value of not larger than 4.5, preferably between 2 and 4.5, most preferably between 3 and 4.5. ClogP is the logarithm of calculated octanol/water partition coefficient.

The amount of fragrance composition employed in perfumed products or articles according to the present invention may vary according to the particular application in which it is employed and on the fragrance loading in the fragrance composition. For detergent applications, one may employ fragrance composition in amounts form 0.01 to 3% by weight of fragrance material based on the total weight of the detergent.

In particular, the microcapsules according to the invention shows high stability and un-preceded perfume retention in consumer products containing 10 to 80 wt % of surfactants, 5 to 90 wt % water, and 0 to 30 wt % hydrophilic excipients such as short chain alcohols, glycol ethers, and short chain polyethylene glycols.

A particular advantage of the microcapsules of the present invention is their combination of two very commercially desirable properties, the ability to retain perfume for long periods in storage, even at elevated temperatures, and high frangibility, allowing ease of release of the perfume when required. In this, they are clearly superior to known microcapsules, wherein decreasing the bursting pressure of the microcapsules is generally accompanied by an increase of perfume leakage from the microcapsules.

The microcapsules according to the invention are especially useful in personal care and household, washing and cleaning products, such as soaps, shampoos, skin care creams, laundry detergents, fabric conditioners, dishwashing liquids, furniture polishes and the like. The invention therefore provides a personal care product, a household product, a washing product or a cleaning product, comprising a composition that comprises microcapsules as hereinabove defined.

The products utilising the microcapsules may be formulated conventionally, using the techniques of and the full range of ancillary materials available to the art. One such ancillary material may be free (non-encapsulated) perfume. Interesting effects can be produced by using a free perfume that is different from the encapsulated perfume in quality and/or strength.

There now follows a series of Examples that serve to illustrate embodiments of the present invention. It will be understood that these Examples are illustrative, and the invention is not to be considered as being restricted thereto.

EX 1

Example of Processes

1.1 Comparative Example According to the Prior Art

The following example illustrates the formation of a standard microcapsule based on melamine-formaldehyde polymer. A solution of 40.5 g of Lupasol PA140 (ex BASF) and various amount (see Table I) of Luracoll SD (methoxy-methylolated melamine pre-condensate (monomer) ex BASF) was added to 250 g of water in a 1 l jacket reactor. The stirring velocity was adjusted to reach the required particles size and the mixture was heated to 35° C. 200 g of perfume (see Table II) were then added to the mixture which was maintained under continuous agitation to allow the formation of an emulsion. The polymerization was started by adjusting the pH value to 3.5 using a 10% solution of formic acid. The reaction was maintained at 35° C. under agitation for 150 minutes. The reaction temperature was then raised to a second temperature T2 (see Table I), in order to achieve complete cross-linking of the microcapsule shell (curing). After 1 hour the pH value was adjusted to pH 2.5 by using a 13% solution of sulfuric acid. The total duration of the curing step was either 75 minutes or 90 minutes (see Table I). The reaction was cooled down and the pH value of the slurry was adjusted to 9.3.

The solid content of the slurry was measured gravimetrically with a Mettler Toledo Halogen Moisture Analyzer HB 43 operating at a constant temperature of 160° C.

TABLE I

Process variation:

| Sample # | Luracoll SD* [g] | Curring time and temperature @° C. | Solid content [wt %] |
|---|---|---|---|
| P1 | 43.5 | 150 min @ 75° C. | 26 |
| P2 | 65.6 | 150 min @ 75° C. | 31 |
| P2.1 | 65.6 | 150 min @ 90° C. | 31 |
| P3 | 65.63 | 180 min @ 90° C. | 32 |

*This number refers to the amount of an aqueous monomer solution containing 70 wt % of active material.

TABLE II

Composition of test perfume oil

| Fragrance Ingredient | Percentage in Formula |
|---|---|
| Verdox | 4.86 |
| anisic aldehyde | 0.73 |
| Benzophenone | 1.46 |
| benzyl acetate | 0.59 |
| benzyl salicylate | 2.88 |
| beta-ionone | 18.85 |
| beta-pinene | 0.45 |
| brassylate ethylene | 0.59 |
| cis-3-hexenyl salicylate | 0.45 |
| Coumarine | 0.59 |
| cyclal C | 2.25 |
| Eugenol | 0.59 |
| Galbanone | 3.47 |
| Habanolide | 0.59 |
| Hedione | 0.59 |
| hexyl acetate | 1.73 |
| hexyl cinnamic aldehyde | 5.76 |
| Iso E super | 11.01 |
| Isoraldeine | 5.10 |
| Lilial | 5.83 |
| Linalol | 1.35 |
| linalyl acetate | 1.46 |
| Nectaryl | 3.47 |
| Oranger | 2.88 |

TABLE II-continued

Composition of test perfume oil

| Fragrance Ingredient | Percentage in Formula |
|---|---|
| beta-decalactone | 3.47 |
| phenyl ethyl acohol | 2.32 |
| prenyl acetate | 1.04 |
| Rosacetol | 1.15 |
| Rosaphen | 0.87 |
| Thibetolide | 0.59 |
| verdyl acetate | 11.28 |
| verdyl propionate | 0.87 |
| Vertofix | 0.87 |
| Total | 100.00 |

1.2 Comparative Examples with Pre-treatment of Monomer

The following example illustrates the formation of a standard polycondensation microcapsule based on melamine-formaldehyde polymer. 43.5 g of Luracoll SD (ex BASF) was pre-treated by heating at 85° C. for 90 min. A solution of 40.5 g of Lupasol PA140 (ex BASF) and the pre-treated Luracoll SD from BASF was added to 250 g of water in a 1 l jacket reactor. The stirring velocity was adjusted to reach the required particles size and the mixture was heated to 35° C. 200 g of perfume were then added to the mixture which was maintained under continuous agitation to allow the formation of an emulsion. The polymerization was started by adjusting the pH value to 3.5 using a 10% solution of formic acid. The reaction was maintained at 35° C. under agitation for 150 minutes. In order to reticulate the shell, the reaction temperature was raised to 75° C. After 1 hour the pH value was adjusted to pH 3.5 by using a formic acid. After 90 minutes the reaction was cooled down and the pH value was adjusted to 9.3 with ammonia. Pre-treatment of the monomer was performed for processes P4.3 and higher.

1.3 Comparative Examples with Co-monomers

The following example illustrates the formation of a modified melamine-formaldehyde microcapsules, using a terpolymer comprising various co-monomer selected from amino compounds, aliphatic polyols and aromatic polyols. A solution of A g (see Table III) of Lupasol PA140 (ex BASF), B g (see Table) and Luracoll SD (ex BASF) was added to 250 g of water in a 1 l jacket reactor. The stirring velocity was adjusted to reach the required particles size and the mixture was heated to a first temperature (35° C.). 200 g of test perfume (table II) were then added to the mixture which was maintained under continuous agitation to allow the formation of an emulsion. The polymerization was started by adjusting the pH value to 3.5 using a 10% solution of formic acid. C g of various co-monomer (see Table IV) was added. The reaction temperature was then raised to 75° C. for 90 minutes, in order to achieve complete cross-linking of the microcapsule shell (curing). After 1 hour curing the pH value was adjusted to pH 3.5 by using a formic acid. After 90 minutes the reaction was cooled down and the pH value was adjusted to 9.3 using ammonia. Table III summarizes typical process variations performed with resorcinol as co-monomer.

TABLE III

Process Variation

| Sample # | A Lupasol Pal40** [g] | B Luracoll SD* [g] | C Resorcinol [g] | Solid content [wt %] |
|---|---|---|---|---|
| P4.0 | 40.5 | 43.5 | 3.06 | 33 |
| P4.01 | 40.5 | 43.5 | 2.30 | 34 |
| P4.1 | 40.5 | 43.5 | 9.18 | 29 |
| P4.2 | 40.5 | 43.5 | 4.59 | 38 |

TABLE III-continued

| | Process Variation | | | |
|---|---|---|---|---|
| Sample # | A Lupasol Pal40** [g] | B Luracoll SD* [g] | C Resorcinol [g] | Solid content [wt %] |
| P4.3. | 40.5 | 43.5 | 6.12 | 33 |
| P4.4 | 40.5 | 58.33 | 6.12 | 34 |
| P5.1 | 40.5 | 26.25 | 3.67 | 31 |
| P5.2 | 24.17 | 26.25 | 3.67 | 37 |

*This number refers to the amount of an aqueous monomer solution containing 70 wt % of active material.
**This number refers to the amount of an aqueous polymer stabilizer solution containing 20 wt % of active material.

TABLE IV

| | Variation of co-monomer | |
|---|---|---|
| Sample # | | Solid content [wt %] |
| | Aliphatic polyol co-monomers | |
| P4.1 | Evernyl | 31.6 |
| P4.1 | 1.4 Cyclohexanedimethanol | 33.2 |
| P4.1 | 1,10 Decandiol | 31.2 |
| P4.1 | Glycerin | <34.2, leakage |
| P4.3 | 2,2 Dimethyl-1,3-propandiol | <31.3, leakage |
| P5.1 | 2,2 Dimethyl-1,3-propandiol | <29.2, leakage |
| P4.3 | 1,1,1,-tris-(hydroxymethyl)-propane | 29.2 |
| P5.1 | 1,1,1,-tris-(hydroxymethyl)-propane | <28, leakage |
| | Aromatic polyols co-monomer | |
| P4.1 | 3,5-dihydroxy-tolulene | 31.50 |
| P4.1 | Pyrocatechol | 37.50 |
| P4.1 | Resorcinol | 37.50 |
| P4.1 | Hydrochinone | 33.00 |

1.4 Cationisation of the Microcapsules

The capsules produced by this method were cationized according to the method described in FR 2 801 811. The capsules were separated from the water phase by adding an 8% solution of sodium chloride and were washed twice with each 550 g of distilled water. After filtration by suction, the filter cake was transferred into a beaker, suspended with 500 g distilled water and cationized with 55.7 g Gafquat HS solution (ex ISP). The mixture was stirred at 300 rpm during 30 minutes

EX 2

Example Relative to Capsule Mechanics

The slurry of suspended microcapsules obtained as in Example 1 is dilutes with deionized water and applied onto a polished and (N2/O$_2$) plasma-cleaned aluminum holder. After evaporation of the water, the holder having discrete microcapsules on its surface is transferred to a MTS Nanoindenter XP equipped with a 60 micrometers diamond flat top indenter body. All compression tests are performed under controlled displacement mode with a displacement rate of 100 nanometer/sec. The load vs. displacement curves are measured to obtain the critical load ($F_{crit}$) and critical displacement ($h_{crit}$) at rupture. Typical results are shown in Table V.

EX 3

Example Relative to Leakage in Fabric Care Softener

Fabric Softener samples containing 1.0 wt % microcapsules comprising encapsulated test perfume and 0.5 wt % free perfume were submitted to 2 months storage at a temperature of 37° C. in sealed glass bottles. 1 g Isolute bulk sorbent Type HM-N (ex Separtis GmbH, Switzerland) was mixed with 10 ml n-Pentane and 2 g of Fabric Softener base. The mixture was stirred during 30 minutes on a magnetic stirrer at maximum speed. After phase separation was completed, the organic phase was transferred into an Eppendorf tube and stored for 15 minutes in a freezer (−18° C.). The cold Eppendorf tube was then centrifuged in an Eppendorf centrifuge at maximum speed for 15 seconds. The clear pentane phase was transferred into GC vial and analysed by split-splitless capillary gas chromatography, without further purification. Typical leakage results are shown in Table V.

TABLE V

| Critical loads at mechanical breakage and perfume loss | | | | |
|---|---|---|---|---|
| Sample # | Luracoll SD level [g] | Resorcinol level [g] | Critical load [mN] | Total perfume loss after storage 37° C./storage time |
| P1 | 43.5 | 0 | 3.9 | 100 wt %/15 days |
| P2 | 65.6 | 0 | 9.8 | 90 wt %/15 days |
| P3 | 65.6 | 0 | 27 | 80 wt %/15 days |
| P4.2 | 43.5 | 4.59 | 10.3 | 11 wt %/2 months |
| P4.1 | 43.5 | 9.18 | 6.7 | 10 wt %/2 months |
| P4.3 | 43.5 | 6.12 | 8.8 | 12 wt %/2 months |
| P5.1 | 26.25 | 3.67 | 4.3 | 20 wt %/2 months |

Comparison of Table I, III, V show that adding co-monomer accordingly to the present invention allows decreasing the critical load required to break the microcapsules to values close to that of the prior art, but using significantly less formaldehyde-containing methylolated melamine, while keeping good perfume retention properties.

EX 4

Determination of Formaldehyde

The residual free formaldehyde level in the microcapsule slurry is determined by high-performance-liquid-chromatography (HPLC) according to Method 8315A of the Environmental Protection Agency (EPA). Hereunto, depending on the expected amount of free formaldehyde, 100 mg to 1 g of slurry is weighted in a 10 ml flask and the volume completed with water. The solution/suspension is exposed for 10 minutes to an ultrasonic bath. The microcapsules are separated from the liquid phase by filtration or centrifugation. Derivatization of the free formaldehyde is achieved by mixing 3 μl of the liquid phase with 6 μl of a solution of 2,4-Dinitro-phenylhydrazine DNPH at 1 wt % in acetonitrile. The analysis is carried out by injecting this mixture in an Agilent 1100 HPLC system equipped with an UV diode-array detector (DAD). Typical results are summarized in Table VI.

TABLE VI

| Impact of polycondensation process on free formaldehyde. See Example 1 for details | | | | |
|---|---|---|---|---|
| Sample # | Luracoll SD [g] | Lupasol PA140 [g] | Resorcinol [g] | HCHO level in the slurry [ppm] |
| P2 | 65.6 | 40.5 | 0 | 2256 |
| P1 | 43.5 | 40.5 | 0 | 660 |
| P4.4 | 58.33 | 40.5 | 6.12 | 409 |
| P4.01 | 43.5 | 40.5 | 2.30 | 285 |
| P4.0 | 43.5 | 40.5 | 6.12 | 118 |

TABLE VI-continued

Impact of polycondensation process on free formaldehyde.
See Example 1 for details

| Sample # | Luracoll SD [g] | Lupasol PA140 [g] | Resorcinol [g] | HCHO level in the slurry [ppm] |
|---|---|---|---|---|
| P4.3 | 43.5 | 40.5 | 6.12 | 100 |
| P4.1 | 43.5 | 40.5 | 9.18 | 73 |
| P5.1 | 26.25 | 40.5 | 3.67 | 35 |

EX 5

Example Relative to Olfactive Evaluation

Laundering trials using microcapsules were performed as follows. European front-loaded wash machines MIELE WT 940 were used, containing 1 kg load consisting of (four) Terry cotton towels (and sometimes cloth from synthetic fibres). 110 g of an unperfumed detergent powder was added. The laundering cycle consisted of (i) a wash cycle at 40° C., using 10-12 liters of water, (ii) 3 rinse cycles, using 12 to 15 liters water per cycle. A fabric softener containing 1.5 wt % microcapsules (0.5 wt % encapsulated perfume) was added in the last rinse. The fabric load was then spin dried at 800 rpm and line dried.

Olfactive evaluation was performed on neat softener, on wet fabrics and on dry fabrics after 1, 5, and 10 days. Evaluation on neat product was carried out to check for possible leakage in the base. Evaluation on the wet fabrics yielded information of the possible breakage of the capsules during the rinse cycle. On dry fabrics, the samples were evaluated before and after rubbing. The fragrance intensity was ranked using a six point scale, as described below:

Intensity 0 No fragrance signal or odour is perceivable
Intensity 1 A very weak fragrance signal or odour that is barely perceivable
Intensity 2 A weak fragrance signal but is perceivable
Intensity 3 Fragrance is perceived easily and is recognisable
Intensity 4 Strong fragrance
Intensity 5 Very strong fragrance

TABLE VII

Olfactive evaluation ratings for softener samples before storage

| Sample # | Neat (flask) | Wet | Dry 1 day* No rub | Dry 5 days* Light rub | Dry 5 days* Heavy rub |
|---|---|---|---|---|---|
| P1 | 2.5 | 3 | 1.5 | 1.5 | 2 |
| P2 | 1 | 1.5 | 0.5 | 1 | 1 |
| P3 | 1 | 1.5 | 0.5 | 0.5 | 1 |
| P4.3 | 0 | 0 | 0 | 1 | 4 |
| P5.2 | 0 | 0 | 0 | 3.5 | 5 |

The invention claimed is:

1. Microcapsules comprising a core of fragrance and a shell of an aminoplast polymer, the composition of the shell being from 75-100% of a thermoset resin comprising 50-90% of a terpolymer and from 10-50% of a polymeric stabilizer; the terpolymer comprising:
   (a) from 20-60% of moieties derived from at least one alkoxylated polyamine,
   (b) from 3-50% of moieties derived from at least one aromatic polyol; and
   (c) from 20-70% of moieties selected from the group consisting of: alkylene moieties and alkylenoxy moieties having 1 to 6 methylene units derived from at least one alkoxylated polyamine;
   the microcapsules additionally optionally comprising up to 25% of a cationic polymer.

2. Microcapsules according to claim 1, in which the polyamine moieties are derived from at least one of: urea, melamine, 3-substituted 1,5-diamino-2,4,6-triazin and glycouril.

3. Microcapsules according to claim 1, in which the aromatic polyol moieties are derived from at least one of: phenol, 3,5-dihydroxy toluene, Bisphenol A, resorcinol, hydroquinone, xylenol, polyhydroxy naphthalene and polyphenols produced by the degradation of cellulose and humic acids.

4. Microcapsules according to claim 1, in which the polymeric stabiliser is an anionic polyelectrolyte.

5. Microcapsules according to claim 1, comprising a cationic polymer selected from the group consisting of: cationic cellulose derivatives, quaternized gums, polyethylene imine, cationic polyacrylates and acrylamides, gelatine, quaternized protein hydrolysates, and quaternized amino silicones.

6. A fragranced personal care, household, washing and cleaning product comprising microcapsules according to claim 1.

7. A product according to claim 6, selected from laundry solid and liquid detergents and liquid fabric softeners and conditioners.

8. A product according to claim 7, in which the product contains free perfume.

9. A product according to claim 8, in which the free perfume differs in strength and/or quality from an encapsulated perfume present in the product.

10. A fabric conditioner according to claim 7, in which the microcapsules are present in an anionic form.

11. Microcapsules according to claim 1, wherein the composition of the shell comprises from 60-85% of said terpolymer.

12. Microcapsules according to claim 1, wherein the composition of the shell comprises 10-25% of a polymeric stabilizer.

13. Microcapsules according to claim 1, wherein the terpolymer comprises 10-25% of at least one polyamine.

14. Microcapsules according to claim 1, wherein the terpolymer comprises 5-25% of moieties derived from at least one aromatic polyol.

15. Microcapsules according to claim 1, wherein the terpolymer comprises
   (c) 40-60% of moieties selected from the group consisting of: alkylene and alkylenoxy moieties having 1 to 6 methylene units.

16. Microcapsules according to claim 1, wherein the terpolymer comprises
   (c) moieties selected from the group consisting of: alkylene and alkylenoxy moieties having 1 to 4 methylene units.

17. Microcapsules according to claim 16, wherein the terpolymer comprises
   (c) alkylene and alkylenoxy moieties having 1 methylene unit.

18. Microcapsules comprising a core of fragrance and a shell of an aminoplast polymer, the composition of the shell being from 75-100% of a thermoset resin comprising 50-90% of a terpolymer and from 10-50% of a polymeric stabilizer; the terpolymer comprising:
   (a) from 20-60% of moieties derived from at least one alkoxylated polyamine, (b) from 3-50% of moieties derived from at least one aromatic polyol; and
(c) from 20-70% of moieties selected from the group consisting of: alkylene and alkylenoxy moieties having 1 to 6 methylene units and which are derived from at least one alkoxylated polyamine;
the microcapsules additionally optionally comprising up to 25% of a cationic polymer.

19. Microcapsules according to claim 18, wherein the cationic polymer is selected from the group consisting of: cationic cellulose derivatives, quaternized gums, polyethylene imine, cationic polyacrylates and acrylamides, gelatine, quaternized protein hydrolysates, and quaternized amino silicones.

* * * * *